United States Patent [19]

Hirleman, Jr.

[11] Patent Number: 5,007,737
[45] Date of Patent: Apr. 16, 1991

[54] PROGRAMMABLE DETECTOR CONFIGURATION FOR FRAUNHOFER DIFFRACTION PARTICLE SIZING INSTRUMENTS

[75] Inventor: Edwin D. Hirleman, Jr., Mesa, Ariz.

[73] Assignee: The United States of America as represented by the Secretary of the Air Force, Washington, D.C.

[21] Appl. No.: 266,952

[22] Filed: Nov. 1, 1988

[51] Int. Cl.$^5$ .............................................. G01N 15/02
[52] U.S. Cl. ..................................... 356/336; 356/335
[58] Field of Search ............................... 356/335–343, 356/561, 356, 432; 250/574, 575

[56] References Cited

FOREIGN PATENT DOCUMENTS 2204678 11/1988 United Kingdom ................. 356/335

Primary Examiner—Vincent P. McGraw
Assistant Examiner—Hoa Pham
Attorney, Agent, or Firm—William G. Auton; Donald J. Singer

[57] ABSTRACT

An intelligent laser diffraction particle sizing system is disclosed. A portion of the primary laser beam is directed by beam splitter into a calibration leg, modulated, and passed through a diffraction reticle. The known diffraction signature of the reticle is then recombined with the primary beam to pass through the particle field. Both the modulated calibration diffraction signature and the portion of the primary beam scattered by the particles are collected by the transform lens and detected at the back focal plane using an X-Y photodiode array. The detector array elements are grouped into variable geometry annular rings. The ring detectors are continuously centered around the beam using feedback from the X-Y position detector which monitors beam deflection.

8 Claims, 5 Drawing Sheets

PROGRAMMABLE DETECTOR CONFIGURATION FOR FRAUNHOFER DIFFRACTION PARTICLE SIZING INSTRUMENTS

STATEMENT OF GOVERNMENT INTEREST

The invention described herein may be manufactured and used by or for the Government for governmental purposes without the payment of any royalty thereon.

CROSS-REFERENCE TO RELATED APPLICATIONS

The subject matter of this application is related to the subject matter contained in the following U.S. patent application Ser. No. 417,150, filed 13 Sept. 1982, entitled: "DEVICE AND METHOD FOR CALIBRATION OF OPTICAL PARTICLE SIZING INSTRUMENTS" which is specifically incorporated herein by reference.

BACKGROUND OF THE INVENTION

The present invention relates generally to particle sizing instruments, and more specifically to a device for determining the particle size distribution in a liquid or a gas using Fraunhofer diffraction patterns.

Many processes would benefit from on-line monitoring of liquid and gaseous suspensions. For example, the ability to characterize the size distribution of dispersed particles and droplets is of crucial importance in a number of practical systems. Some important applications include liquid fuel droplets sprayed into air in combustion systems such as boilers and gas turbine combustors; solid particles dispersed in liquids as in coal-oil slurries; solid particles dispersed in combustion exhausts with respect to the health aspects of particulate pollutant emissions; and others. In many of these applications optical (as opposed to batch) sampling techniques for particle sizing are advantageous and sometimes necessary. (The term particle will refer herein to both solid particulate matter and liquid droplets of diameters approximately 0.01 μm to 1 mm.)

A problem which is often encountered in measuring techniques is to determine the size distribution of physical entities, such as particles in a liquid or gas. This task is alleviated, to some extent, by the systems described in the following U.S. Patents, the disclosures of which are specifically incorporated herein by reference:

U.S. Pat. No. 3,469,921 issued to Taylor;
U.S. Pat. No. 3,636,367 issued to Girard;
U.S. Pat. No. 4,037,964 issued to Wertheimer et al;
U.S. Pat. No. 4,338,030 issued to Loos;
U.S. Pat. No. 4,251,733 issued to Hirleman;
U.S. Pat. No. 4,188,121 issued to Hirleman;
U.S. Pat. No. 3,835,315 issued to Gravitt;
U.S. Pat. No. 3,689,772 issued to George et al;
U.S. Pat. No. 3,988,612 issued to Palmer;
U.S. Pat. No. 4,360,799 issued to Leighty; and
U.S. Pat. No. 4,740,677 issued to Carreras et al.

Advanced optical systems for determining the particle parameter of size often use laser illumination of single particles and analysis of the scattered light characteristics to obtain information on the size and other physical parameters of a given particle. The sizes of many particles are measured and summed to determine an overall particulate size distribution. The use of lasers is advantageous due to the greater light intensity available as compared to conventional light sources, thereby allowing measurement of smaller particles and enhancing the ability for in-situ or non-interfering measurements. Arrangements using white light scattered in only one solid angle require an extremely well defined and compact sampling volume through which a representative sample of the particulate flow must be passed.

In the system disclosed by Gravitt, laser or other light is focused to intensely illuminate a small region in space. This region, called the sensitive volume or particle sampling zone, is located in the field of light collecting apparatus which discriminates between the light scattered at two small angles and the light traveling in the light beam propagation direction. Detector means are used simultaneously to detect and record signals representing the intensities of the scattered light detected at the different angles. A measure of one of the parameters, i.e. the particle size, of a particle passing through the sampling zone is determined by measuring the ratio of the signals representing the intensities of the scattered light detected at two angles. This measurement is, however, non-unique or ambiguous since particles of different sizes may pass through the sampling zone and since many particle sizes can generate the same ratio signal.

One problem with a laser system is the Gaussian intensity distribution in the beam, since single angle systems can not differentiate between a small particle passing through the high-intensity center of the beam and a larger particle passing through an off-center point of lower intensity. This problem can be eliminated by utilizing the ratio of light intensities scattered in two directions thereby cancelling the incident intensity effect as suggested by Gravitt.

Since the Fraunhofer diffraction pattern possesses circular symmetry, the rings and wedges sample the diffracted energy in polar coordinate form. That is, the rings sample the distance of the diffraction pattern portions from the axis, while the wedges sample the direction at which portions of the pattern are disposed. A suitable wedge-ring Detector, having 32 rings and 32 wedges, is disclosed in U.S. Pat. No. 3,689,772, and is manufactured by Recognition Systems, Inc. of Van Nuys, Calif.

The above-cited Palmer reference discloses a photodetector array system, which is an array which is comprised of a matrix of photodiode detectors, and may for instance be a 32 by 32 element device such as the Reticon model R32X32A.

The first of the above-cited Hirleman patents disclose a technique for measuring particle size and velocity, using two beams of electromagnetic radiation with symmetric radial intensity distributions are directed through space. A particle sampling volume is defined by those portions of the two beams within the field of view of one or more radiation sensitive detectors. The detectors respond to scattered radiation or fluorescence from particles passing through the beams in the sampling volume. The detector output for a single particle indicates two signal pulses corresponding to those times when the particle was in one of the beams. The speed of the particle in the plane perpendicular to the beams is determined from the transit time or width of the signal pulses, and the angle of the particle traverse in that plane determined from the time-of-flight between the signal pulses.

The second of the above-cited Hirleman patents is an improved multiple ratio single particle counter. Intensities of scattered radiation are measured at more than two angles and ratios of these intensities are derived. These ratios are compared with calibration curves to determine an unambiguous measure of the particle parameter.

Loos shows an arrangement for measuring the size distribution of particles suspended in a gas or in a liquid. In this patent a spatial filter is placed in the exit plane of a dispersive element so that its transmittance is a function of position on the filter. Light transmitted by the filter is measured by a photodetector. The photodetector output is measured as different spatial filters are switched in place.

Wertheimer et al discuss a Fraunhofer plane spatial filter in which a mask lies in the Fraunhofer plane of lens. In Taylor size distribution of an aggregation is determined by the amount of light in a ring in the Fourier plane. Girard describes a Fourier transform optical analyzer which uses a mask shifted step by step relative to an optical object support.

While the above-cited references are instructive, the task of measuring particle size distribution in liquids and in gas remains an ongoing need. The present invention is intended to make a useful contribution towards satisfying that need.

SUMMARY OF THE INVENTION

The present invention includes a device for determining the particle size distribution in a liquid or a gas using Fraunhofer diffraction patterns. It involves placing a mask or filter in the transform plane before a single light detector. The mask is an array of light valve elements (pixels), each of which can be independently programmed to either the transmitting (transparent) or absorbing (opaque) state. This programmable light valve array can be of any geometry. Thus an instrument with some level of intelligence can interrogate the scattering pattern, determine those scattering angles at which the particle size information is maximized, and then reconfigure the detector to sample more points (scattering angles) in those regions of most interest.

It is an object of the present invention to provide a system for determining particle size distribution in liquids and gases.

It is another object of the invention to provide a particle sizing instrument using a light valve array in the transform plane, and using Fraunhofer diffraction patterns.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present invention is a device for determining the particle size distribution in a liquid or a gas using Fraunhofer diffraction patterns. Fraunhofer diffraction may be defined as the field transmitted through an aperture in an absorbing screen. It is concerned with the field pattern at large distances from the screen, so that waves from the virtual sources at the aperture arrive in phase at a point normal to the screen.

Figure 1:
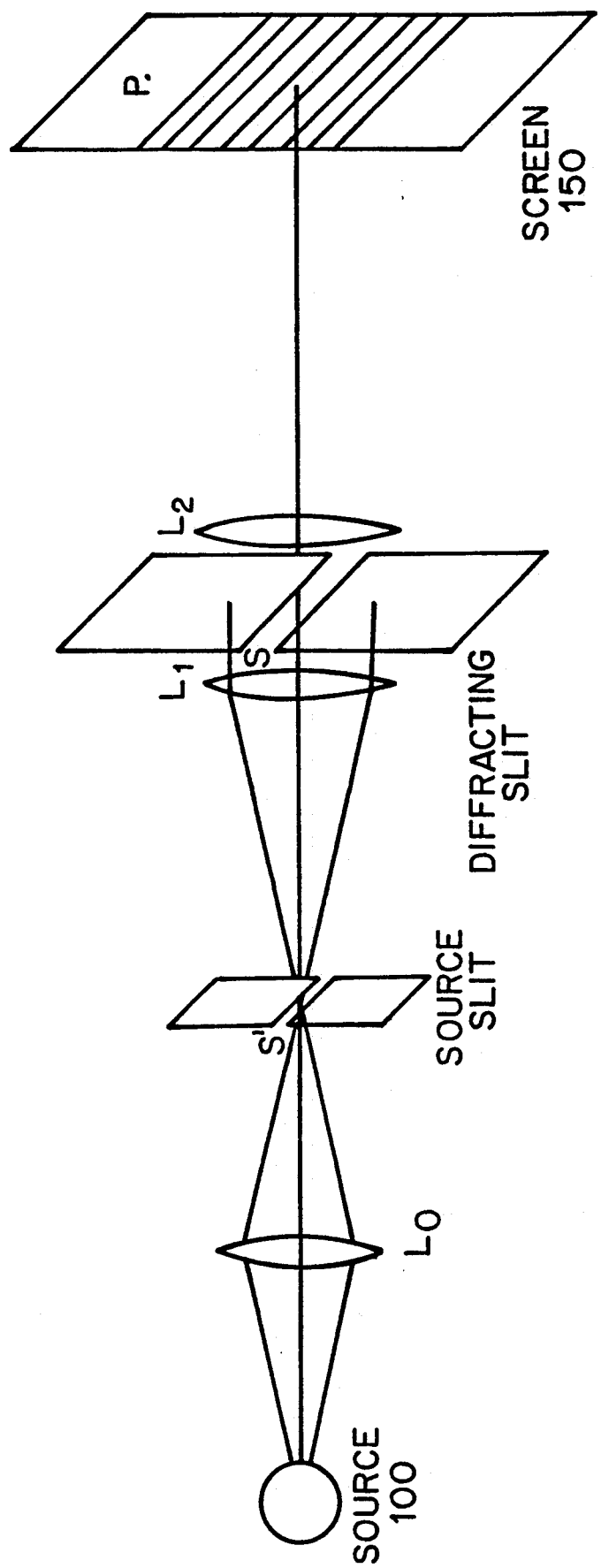
FIG. 1 is an illustration of a Fraunhofer diffraction system.

The readers attention is now directed towards FIG. 1, which is an illustration of a Fraunhofer diffraction system manifested in the diffraction pattern of a single slit. As shown in FIG. 1, when a beam of light passes through a narrow slit, it spreads out to a certain extent into the region of the geometrical shadow. This effect, is one of the simplest examples of diffraction, i.e., of the failure of light to travel in straight lines. Fraunhofer diffraction is observed in practice by rendering the light from a source parallel with a lens, and focusing it on a screen with another lens placed behind the aperture, an arrangement which effectively removes the source and screen to infinity.

In FIG. 1, a Fraunhofer diffraction pattern is established using a source 100, source lens $L_0$, a source slit S', a diffracting slit S, two lenses $L_1$ and $L_2$, and a screen 150. When slit S is set up as in FIG. 1 with its long dimension perpendicular to the plane of the page, and is illuminated by parallel monochromatic light from the narrow slit S', at the principal focus of the lens $L_1$, the light focused by another lens $L_2$ on a screen or photographic plate P at its principal focus will form a diffraction pattern, as indicated schematically.

Figure 2:
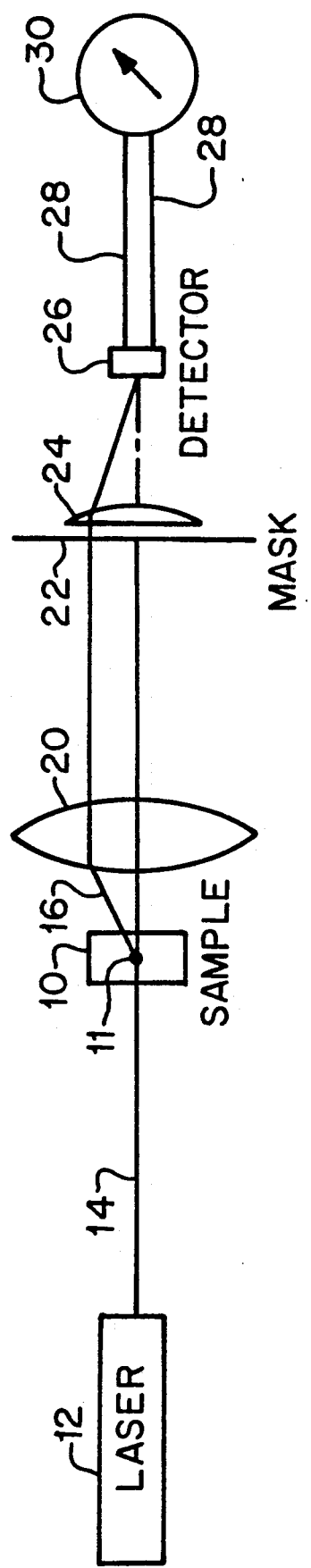
FIG. 2 is a prior-art system which uses Fraunhofer diffraction to detect the size of particles.

The reader's attention is now directed towards FIG. 2, which is a prior-art system which depicts how Fraunhofer diffraction can be used to detect the size of particles. FIG. 2 is an illustration of the above-cited Wertheimer et al system in which a Fraunhofer plane spatial filter is used in filtering the forward scattered light from a collection of particles to obtain an indication of the sum of the radii of the particles as a direct function of the total diffracted light flux passed by the filter.

In the system of FIG. 2, the collection of particles forming the sample in container 10 may, for example, be a sample of fluid suspended particles either contained within an enclosure or in a flowing stream. That sample is placed in a position such that a collimated light beam is directed at the particles as by the laser 12 which is shown in FIG. 1 directing a light beam 14 along the optical axis of the system. Particles such as particle 11 which are in the sample collection 10 and lie in the path of the light beam 14 cause a diffraction of the light beam at an angle as for example along path 16. The diffracted light is directed by a focusing element which consists of the collecting lens 20 through the mask 22 which lies in the Fraunhofer plane of lens 20. That portion of the diffracted light which passes through the mask 22 is focused by the lens 24 on detector 26. The detector 26 in turn produces on its output lines 28 a signal into indicator 30 indicative of the total light flux falling on the detector 26.

Figure 3:
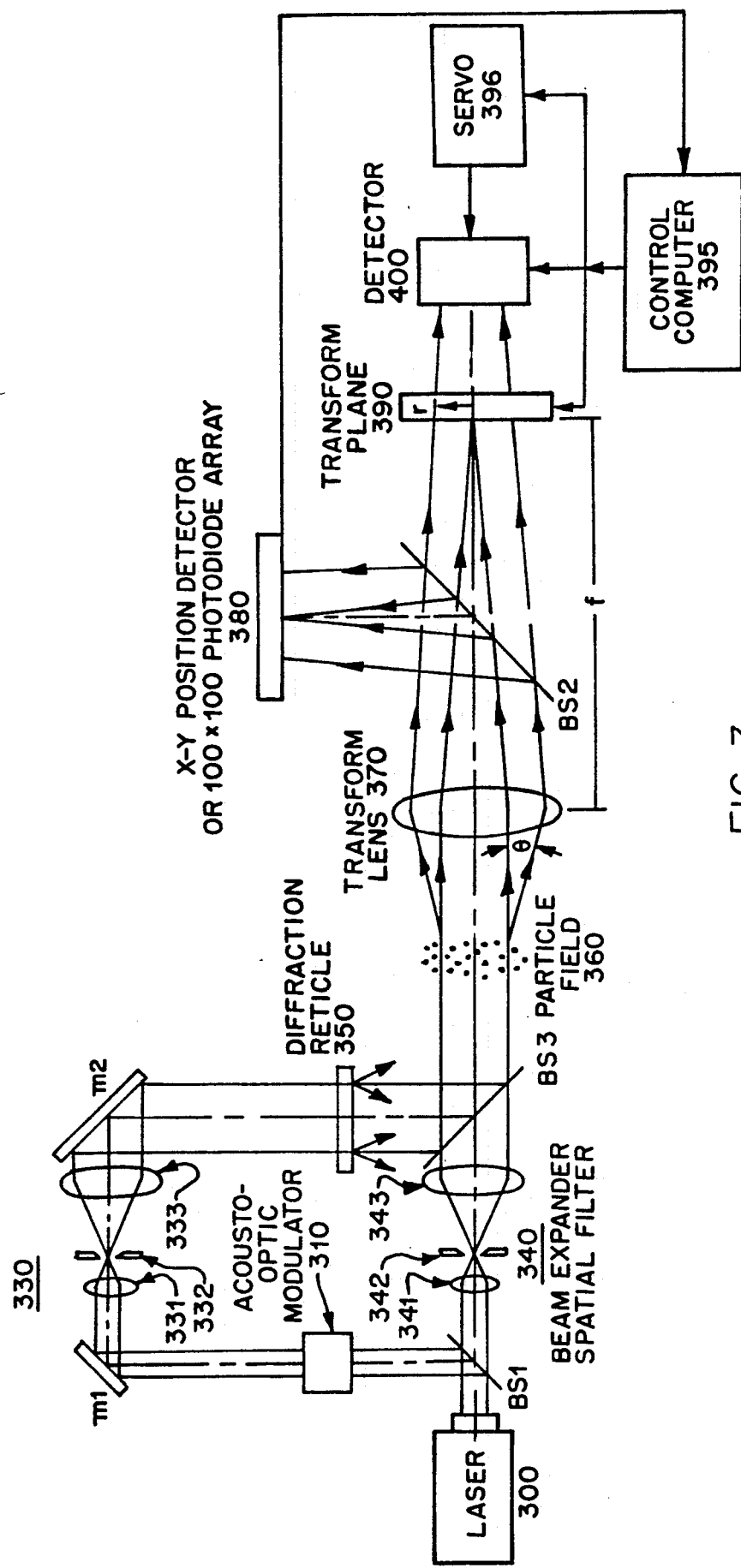
FIG. 3 is a schematic of the present invention.

FIG. 3 is a schematic of the laser diffraction particle sizing system of the present invention. The system of FIG. 3 can be used to determine the particle size distribution in a liquid or gas from Fraunhofer diffraction patterns, using: a laser 300, an acousto-optic modulator 310, two mirrors M1 and M2, two beam splitters BS1, BS2, two beam expander spatial filters 330, 340, a diffraction reticle 350, a transform lens 370, a position detector 380, a transform plane 390 and a detector 400.

All of the elements of FIG. 3 are commercially available units, and can be used to determine the particle size distribution in a liquid or a gas using Fraunhofer diffraction patterns. It involves placing a mask or filter in the transform plane 390 before a single light detector 400. The mask is an array of light valve elements (pixels), each of which can be independently programmed to either the transmitting (transparent) or absorbing (opaque) state. This programmable light valve array can be of any geometry. Thus an instrument with some level of intelligence can interrogate the scattering pattern, determine those scattering angles at which the particle size information is maximized, and then reconfigure the detector to sample more points (scattering angles) in those regions of most interest.

In FIG. 3, the laser 300 emits an illuminating beam which is split by the first beam splitter BS1. Part of the beam is modulated by the acousto-optic modulator 310 to produce a modulated beam, and part of the original illuminating beam is processed by the first beam expander spatial filter 340.

Each of the two beam expander spatial filters 330 and 340 operate in the same manner as the diffracting slit S and two lens elements $L_1$ and $L_2$ of FIG. 1. For example the first beam expander spatial filter 340 has a first lens 341 which will focus the illuminating beam from the beam splitter BS1 onto the center of the diffracting slit 342. The second lens 343 will receive and focus the resulting Fraunhofer diffraction pattern on the beam combiner BS3.

Please note the acousto-optic modulator 310, the second beam expander spatial filter 330 and diffraction reticle 350 optional components of the present invention. These serve as an on-line calibration test system as described in the above-cited patent application, and as requested in the manner described below.

The acousto-optic modulator 310 receives and modulates the laser beam from the first beam splitter in order to produce a modulated laser beam signal which is distinguishable from the output of the laser 300. Accordingly, the first beam spliter BS1 is providing the acousto-optic modulator 310 with a sample of the illuminating beam of the laser 300. The acousto-optic modulator receives and modulates the sample of the illuminating beam to produce thereby a modulated sample of the illuminating beam. Next, the first mirror m1 directs the modulated sample laser beam from the acousto-optic modulator 310 into the second beam expander spatial filter 330, whose two lenses 331 and 333 along with its diffracting slit 332 produce a Fraunhofer diffraction pattern from the modulated beam. The second beam expander spatial filter 330 receives and expands the modulated sample of the illuminating beam through a second slit to produce an output which includes a Fraunhofer diffraction pattern of the modulated sample of the illuminating beam of the laser 300. This is directed by the second mirror m2 through the diffraction reticle to the beam combine BS3.

Figure 4:
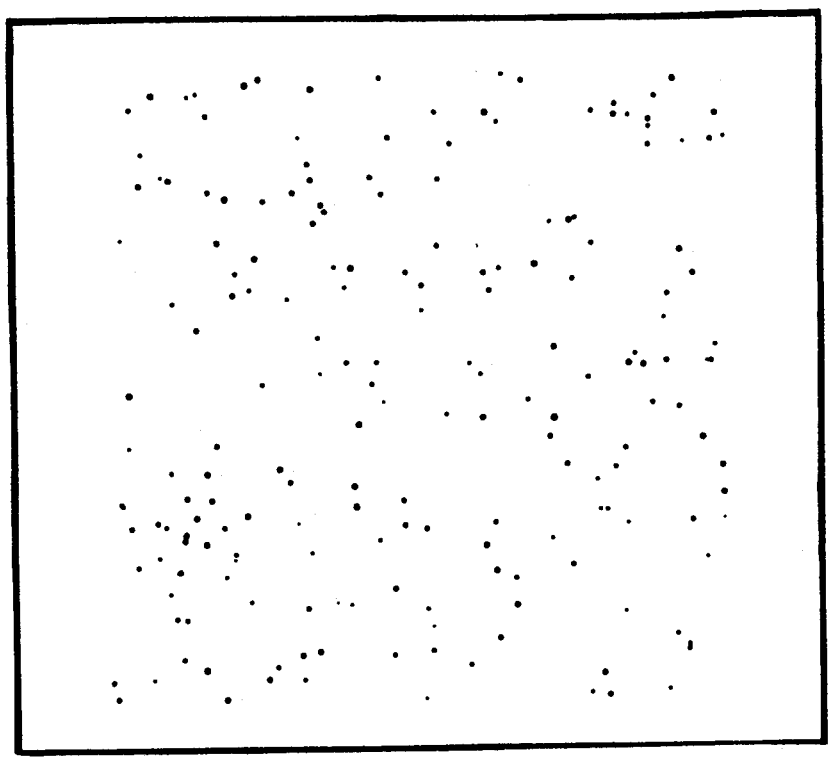
FIG. 4 is an illustration of a diffraction reticle as used in FIG. 3.

FIG. 4 is an illustration of a diffraction reticle which is taken from the above-cited patent application. The reticle 350 is a transparent sheet which simulates a known particle size distribution with a particle array of randomly positioned circular apertures are etched in substantially opaque thin films deposited on a substantially transparent substrate. Since the detector 400 outputs an indication of the detected particle size distribution of the reticle, this can be compared to its known particle size distribution characteristics to determine the accuracy of the system. The acouso-optic modulator 310 can simply be turned off if the testing feature is not required.

The beam combiner BS3 outputs a combined Fraunhofer diffraction beam by combining the Fraunhofer diffraction pattern of the modulated laser beam with the Fraunhofer diffraction pattern of the original laser beam. This combined Fraunhofer diffraction pattern is directed through the particle field of interest 360 where it is focused by the transform lens 370 onto the second beam splitter BS2. In the system of FIG. 3, the transform plane 390 is fixed in the focal point of the transform lens 370.

The second beam splitter splits the combined Fraunhofer diffraction pattern so that fifty percent of it is sent to the X-Y position detector 380, and the rest is sent through the transform plane 390 to the detector 400. The present invention uses two detectors on the combined Fraunhofer diffraction pattern as follows. The single light detector 400 collects forward scattered light from the particles in the particle field 360 to obtain an indication of the sum of the radii of the particles as a direct function of the total diffracted light flux. This measurement principle is demonstrated in the above-cited Wertheimer et al patent and is understood in the art.

The photodiode array 380 is an array of multiple light-sensitive detectors which act as an X-Y position detector. Examples for a suitable photodiode array are described in the Palmer patent, and in such standard texts as "Optical Radiation Detectors" by E. L. Dereniak et al which was published in New York by John Wiley & Sons, the disclosure of which is incorporated herein by reference. Each individual detector will indicate if it is detecting light or not. The collective output of the photodiode array will indicate the position of the center of the laser beam and forward this information to the system control computer 395.

The system control computer 395 is able to determine center of the laser beam from a pattern-recognition program similar to that used in the above-cited Leighty patent. As mentioned above, each photoconducting element of the photodiode array will indicate whether or not it is receiving light from the laser beam. Collectively, the photodiode array 380 depicts a two dimensional representation of the position of the laser beam, which is sent to the control computer 395. The control computer 395 responds by directing the servomechanism 396 to tip or tilt the detector 400 so that it is directed at the center of the laser from the transform lens 370. The above-cited Carreras et al patent provides a suitable servomechanism in the form of three piezoelectric transducers. As shown by Carreras et al, these piezoelectric transducers expand when receiving electricity to compensate for X and Y tilt error-signals. The programming of control computer 395 to accomplish the above-described data-recording operations is routine, and within the skill of one in the art. The control computer for example, may be a Hewlett-Packard HP2112 mini-computer running under the RTE IV operating system.

In addition to controlling the servomechanism 396, the computer 395 can adjust the transform plane 390 as follows., First, note that the element that is in use in the transform plane 390 is a commercially-available spatial light modulator. Such use was described by Mr. Hirleman et al in their article entitled "Faraday-effect Light Valve Arrays for Adaptive Optical Instruments", as published in Volume 63 of ICALEO by the Laser Institute of America in 1987, the disclosure of which is incorporated herein by reference, and repeated in part below.

Spatial light modulators(SLM), in the most general sense, are devices which produce a spatial variation of the optical properties of a light beam or field. One common mode of operation of an SLM involves conversion of electronic information (e.g. stored in a digital electronic computer) to optical information as represented by a spatial variation of optical properties. In other cases such as in an all optical computer, the conversion is between two forms of optical information. An SLM may be used to create specified spatial variations in optical intensity, state of polarization, or spectral content.

Figure 5:
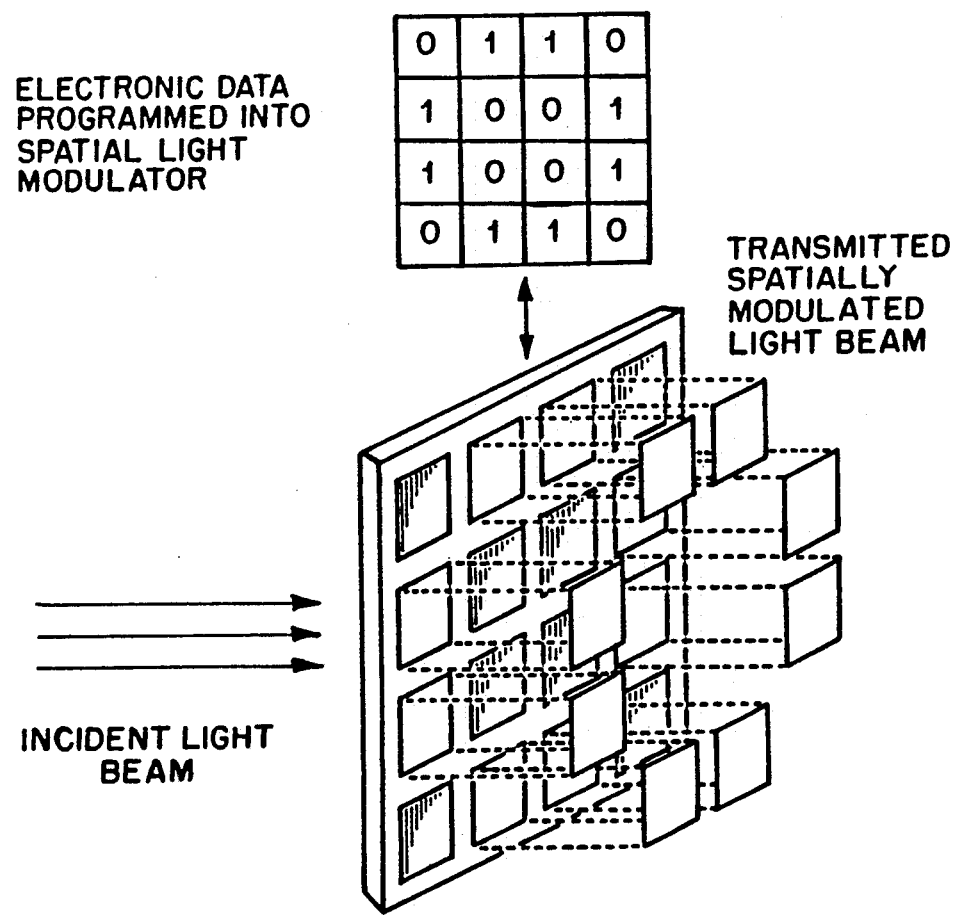
FIGS. 5 and 6 are detailed illustrations of the features of the spatial light modulator used at the transform plane of the system of FIG. 3.

The modulated optical field is often formed by using the SLM in a transmission mode, i.e. where a light beam of initially uniform properties is passed through the modulator and different regions of the beam leave with specified changes in optical properties. In FIG. 5, the scheme for implementing a two-dimensional transmission mode SLM is shown where the pixels either totally absorb or totally transmit the incident light. Another configuration involves operation in the reflective mode, where an incident (uniform) beam is directed onto the SLM and the reflected beam is spatially altered., While the example in FIG. 5 indicates electronic control of the SLM, it is also possible to switch the pixels using optical rather than electronic stimuli.

FIG. 5 is a schematic of an idealized two dimensional spatial light modulator operated in a binary transmission absorption mode. The pixels are programmed according to the array of binary data, and the optical energy incident on a pixel is either totally transmitted or totally absorbed.

Figure 6:
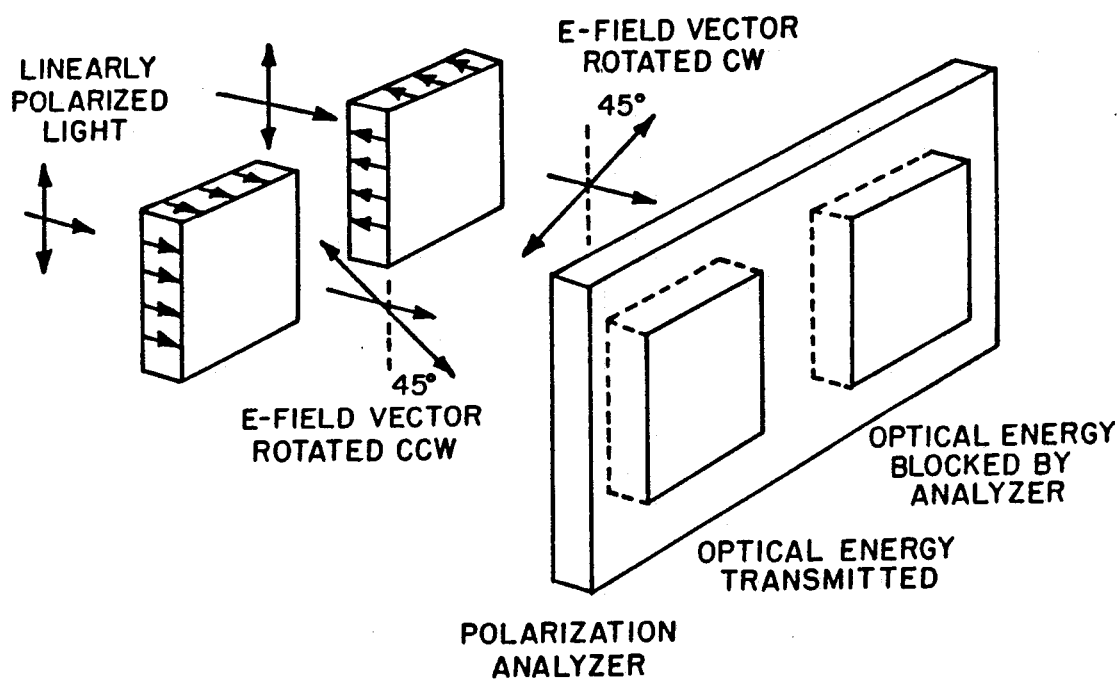

The particular SLM types which might be used are determined by the application. Our research is concerned with diagnostic instruments for particle-laden flows. Typical maximum frequencies of interest are in the 10 kHz range, and spatial dynamic ranges of the order of 100 and greater are required. The commercial SLM which came the closest to satisfying our constraints is a magneto-optic device which uses the Faraday effect to selectively alter the polarization vector of incident light transmitted through the modulator material. A schematic of two example pixels of the SLM as used in our application is shown in FIG. 6.

Returning to FIG. 3, the spatial light modulator of the transform plane 390 is used to create programmable detector geometries which can be optimized depending on the particular particle size distribution under analysis. In FIG. 3, we are investigating laser diffraction particle sizing where the angular distribution of scattered light is collected at multiple angles for use in an inverse scattering calculation.

In the present invention, annular ring openings are created in the SLM at the transform plane by setting the pixels to transmit or block the incident polarized light. The field detector collects all light passing through the SLM, and is sequenced through the optimal number of rings at optimal locations. In this manner, the SLM at the transform plane 390 acts as a programmable transmission filter which selects desired angular distribution of scattered light to be received by the detector 400. This is important since light scattered by relatively large particles in the particle field 360 is concentrated in very small angles near the center of the axis of the incident radiation. Light scattered by small particles goes into comparatively large angles, and is received by the detector 400 further off the center of the axis of the incident radiation. These general principles are incorporated into the particle sizing strategy by the system of FIG. 3 in the manner discussed below.

In the system of FIG. 3, the X-Y position detector 380 provides the control computer with the location of the center of the beam from the transform lens 370, in the manner described above. Next, the control computer 395 directs the servomechanism 396 to adjust the detector 400 towards the center of the beam using three piezoelectric transducers to eliminate tilt error angles (as shown by Carreras et al).

Figure 7:
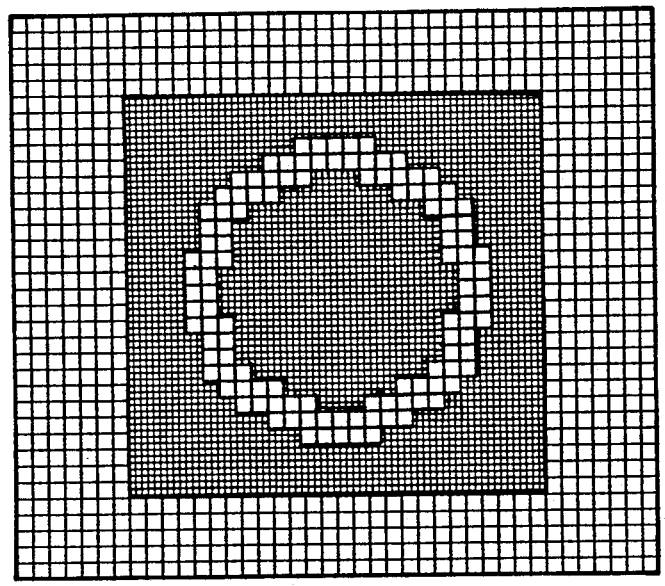
FIG. 7 is an illustration of the mask pattern generated by the spatial light modulator when used in the system of FIG. 3.

Now that the detector 400 is aligned with the center of the axis of incident radiation, the control computer 395 selectively activates the spatial light modulator of the transform plane 390 to present a mask with annular transparent ring shapes which are incrementally increased in radius and thickness. This allows the detector to selectively detect particle size distributions of immediate interest. Pixels are opened in groups which form rings of concentric circles about the optical axis of the beam on the transform plane, as shown in FIG. 7. Suitable spatial light modulators, which are commercially available, are listed below along with their operating characteristics in Table 1.

TABLE 1

| | Spatial Light Modulators | | | | | |
|---|---|---|---|---|---|---|
| Device | Optical Effect | Contrast Ratio | Switching Time (sec) | Control | Pixel Size | Array Size |
| CCD-LCLV | Birefringence | $10^2$ | $10^{-1}(10^3)$ | Elec | 20 $\mu$m | 256 × 256 |
| Deformable Surface | Surface | $4 \times 10^2$ | $10^{-2}$ | Optical | 100 $\mu$m | 300 × 200 |
| Ferroelectric LC (InSnO) | Birefringence | $10^2(10^3)$ | $10^{-6}-10^{-4}$ | Elec | 17 $\mu$m | 32 × 32 |
| Magneto-optic (Fegamet) | Birefringence | $10^3(10^5)$ | $10^{-7}$ | Elec | 76 $\mu$m | 128 × 128 |
| QCSE-SEED (GaAs-GaSlAs) | Absorption | $10^1(10^2)$ | $10^{-10}$ | Elec/Opt | 60 $\mu$m | 6 × 6 |
| Si PZLT | Refractive | $10^2$ | $10^{-5}$ | Optical | 100 $\mu$m | 16 × 1 |

TABLE 1-continued

| Device | Spatial Light Modulators | | | | | |
|---|---|---|---|---|---|---|
| | Optical Effect | Contrast Ratio | Switching Time (sec) | Control | Pixel Size | Array Size |
| | Ind. | | | | | |

In Fraunhofer diffraction particle sizing it is necessary to measure light scattering at a multiplicity of angles to infer particle size distribution of information. Generally the optical system of FIG. 3 is used where a transform lens converts the farfield angular diffraction pattern into a spatial distribution of scattered light at the transform or detection plane. In the prior art there have been number of concepts developed for sampling the scattering or diffraction pattern. In the earliest work researchers translated a single detector with a pinhole aperture across the diffraction pattern to obtain measurements at roughly even increments of scattering angle. A major shortcoming of this technique is the fact that the intensity in the diffraction pattern drops off rapidly from the near-forward (near on-axis) angles to larger off-axis angles. This results in a signal dynamic range which is often too large for a single detector in practical environments where noise is a problem. Similar difficulties are encountered when a solid state detector array with equal are detector elements is used.

A very general method to compress the dynamic range required of detectors in a laser diffraction system is to utilize detection strategy whereby the detector aperture(s) increase in area as the distance from the diffraction pattern center is increased. This approach provides the largest area over which the detector is integrating in those regions of the diffraction pattern where the intensity is lowest. One embodiment of this approach suggested by Wertheimer et al. [1977] uses a combination of rotating and stationary masks at the transform plane to create a series of apertures which transmit light to a field detector located behind the transform Plane. The moving mechanical parts in the system of Wertheimer et al. [1977] are a significant disadvantage and a similar effect can be achieved by using an array of concentric annular detectors on a single silicon wafer with areas which increase with radial distance from the detector center as suggested in a patent by George et al. [1972]. The detector of George et al., [1972], which had a series of semiconductor annular ring elements on one half and a series of wedge-shaped detector elements on the other half, was manufactured by Recogntion Systems Inc. (RSI).

Use of this detector geometry for Fraunhofer diffraction particle sizing was suggested by Swithenbank et al. [1977]. Note however that Swinthenbank et al. [1977] adopted the existing detector geometry of RSI which had detector sizes increasing with distance from the detector center, but made no reference to the mathematical relations or formula which should govern the specific dimensions of the various detector elements. Note also that George et al. [1972] patented a particular geometry which had both rings and a set of wedge-shaped detectors, and they also made no reference to any logical or mathematical means for specifying the exact detector geometry such as represented by values of the ring detector inner and outer diameters.

This invention uses an algorithm or set of mathematical formula which allow the specification of an optimal detector geometry for a ring detector to be used in laser Fraunhofer diffraction particle sizing applications. In particular, based on developments in the above-cited abstract by Hirleman [1986] it is shown that the optimal detector should have elements which have areas proportional to the scattering angle $\theta^2$. For detectors which follow this geometry, the output signal level S will be given by:

$$S \alpha I(\theta) \cdot Area \alpha I(\theta) \cdot \theta^2 \qquad (1)$$

where $I(\theta)$ equals the scattering intensity at scattering angle $\theta$

The detector scaling law of Eq. 1 can, in turn, be satisfied by ring detectors as in FIG. 3 where each annular element (e.g. the ith) has a constant ratio of outer radius $r_o,i$ to inner radius $r_i,i$ (Note that r in the transform plane is proportional to scattering angle $\theta$ for the small scattering angles used in Fraunhofer diffraction systems, $r = f\theta$ where f is the transform lens focal length and r equals the radial distance measured from the center of the diffraction pattern). The detector scaling relations then become:

$$r_{o,i}/r_{i,i} = \theta_{o,i}/\theta_{i,i} = C_d \text{ (a constant)} \qquad (2a)$$

$$\bar{r}_{i+1}/\bar{r}_i = \bar{\theta}_{i+1}/\bar{\theta}_i = C_d \qquad (2b)$$

$$\bar{r}_i/r_{i,i} = \bar{\theta}_i/\theta_{i,i} = (C_d)^{\frac{1}{2}} \qquad (2c)$$

where the overbar indicates mean quantities representative for finite aperture detector and where:

$r_i$ equals the radial distance measured from the center of the diffraction pattern measured from the $i^{th}$ detector for a finite aperture detector;

$r_{i+1}$ equals the radial distance measured from the center of the diffraction pattern to the $i+1^{th}$ detector for a finite aperture detector;

$r_{i,i}$ equals the inner radius of each annular element, $r_{o,i}$ equals the outer radius of each annular element;

$\theta_i$ equals the scattering angle with respect to the $i^{th}$ detector element;

$\bar{\theta}_i$, equals the scattering angle with respect to the ith detector element for a finite aperture detector; and $\theta_{i,i}$ equals the scattering angle with respect to the inner radius of the annular ring detector. Now the system equation can be written in matrix form as:

$$S = C \cdot A \qquad (3)$$

where S, A, and C are matrices such that S is the scattering signal on the ith detector (representative angle $\theta_i$), Aj is the particulate area in the jth size class (of representative size $a_j$) and the C matrix is the scattering cross section for the radiation received by the detector which is given by $C_{ij}$, which is defined as:

$$C_{ij} = J_1 2(a_j \theta_i) \qquad (4)$$

In equation 4, $J_1$ is a Bessel function of the first kind and first order, and is squared. As mentioned above, $\bar{a}_j$ is the particle size parameter $\alpha$ representative of the $j^{th}$ discrete particle class size for a finite aperture detector.

Note that Eq. (4) is valid for only the simplest quadrature scheme (rectangular) but will demonstrate the principle and can be implemented for more complex quadrature schemes.

At this point the diameter ranges covered by the various size classes are still undetermined; the only constraint is that the number of size classes must be n or less (where n is the number of detectors). If we also set:

$$\bar{a}_j/\bar{a}_{j+1}=C_d \quad (5)$$

which makes o the largest size class then:

$$C_{ij}=J_1 2(C_d{}^{i-j}\bar{a}_o\bar{\theta}_o) \quad (6)$$

whereby all elements on any diagonal ($i-j$=constant) in the C matrix are equal and therefore have the same value, and therefore there only $2n+1$ unique elements in C. The C matrix is the scattering cross section for the radiation received by the detector, as described above. Clearly this drastically reduces the computational complexity since the storage requirements have decreased from $O(n^2)$ to $O(n)$. Further, if n values of are selected according to Eq (5) with the additional constraint of maximizing the signal S on a corresponding detector as given by:

$$\bar{a}_o \cdot \bar{\theta}_o = 1.84 \quad (7)$$

which is the argument value which maximizes $J_1 2$, then the C matrix has the largest elements on the diagonal and for small enough n will always be diagonally dominant. This optimizes the condition number of the instrument function C matrix and therefore the stability, robustness, and noise immunity of the inversion required for determination of the size distribution.

In summary, this invention comprises optimal scaling laws for the detector configuration and size classes for Fraunhofer diffraction particle sizing instruments. The detector elements should be concentric annular rings with inner and out radii governed by Eq. (2a). The relative positions of the size classes in particle size space should be similarly log-scaled as given Eq. (5), and the absolute value of the size class centers corresponding to each annular detector should be fixed by Eq. (7). Fraunhofer diffraction particle sizing instruments designed using the scaling laws disclosed here will have significant advantages over instruments designed with prior art in terms of accuracy and stability.

Further information on particle sizing characteristics is available in the following technical articles, the disclosures of which are specifically incorporated herein by reference:

1. Hireleman, E. D. and Koo, J. H. "Research on Certain Aspects of Laser Diffraction Particle Size Analysis Relevant to Autonomous, Self-diagnosing Instrumentation", Research Progress and Forecast Report, Apr. 18, 1986.
2. Hireleman, E. D. land Koo, J. H. "Research on Certain Aspects of Laser Diffraction Particle Size Analysis Relevant to Autonomous, Self-diagnosing Instrumentation", copy of Abstract included in Book of Abstracts for AFOSR Contractors Meeting, June, 1987, Penn State University.
3. Hireleman, E. D. and Koo, J. H. "Research on Certain Aspects of Laser Diffraction Particle Size Analysis Relevant to Autonomous, Self-diagnosing Instrumentation", pp. 45-48 in Book of Abstracts for AFOSR Contractors Meeting, June 16-17, 1986, Stanford University.

As mentioned above, in Fraunhofer diffraction particle sizing it is necessary to measure light scattering at a multiplicity of angles to infer particle size distribution information. Generally the optical system of FIG. 3 is used where a transform lens 370 converts the farfield angular diffraction pattern into a spatial distribution of scattered light at the transform or detection plane 390. The diffraction pattern is then sampled at the transform plane 390 using, in most state-of-the-art systems, a multi-element photodiode detector array 380. Unfortunately, the optimal detection strategy (i.e. the definition of exactly which scattering angles and associated collection apertures should the detectors be oriented in order to extract the most information about the particle size distribution) depends on the size distribution which is obviously not known before the measurement. Prior art for Fraunhofer diffraction instruments have used fixed detector geometries which are, therefore, not in general optimized for any particular measurement. This invention suggests a method by which the arrangement of the detectors is variable and therefore can be changed on-line to a configuration optimized for the instantaneous measurement context. The basic concept is shown in FIG. 3 where a transform plane mask with a nominally square array of "light valve" elements (pixels) is shown. In this invention each pixel can be independently programmed to one of two states: transmitting (transparent) or absorbing (opaque). When a pixel is switched to the transmitting state then any light incident on it will be transmitted nominally unattenuated to the detector 400 following the transform plane 390, and when any one pixel is switched to the absorbing state then any light incident on it will be absorbed and not transmitted.

Note that a detector array could be used at the transform plane 390 in place of the transmission masks pattern and the subsequent field detector 400, and the signals from these detectors grouped in various ways on-line to produce the same functionality as this invention. However, the present invention is significantly better because in the other scenario each of the multiple detectors must be individually sampled (requiring long times) and each will add an additional noise contribution. The single detector 400 required for this invention introduces only one noise contribution and must be sampled only once per grouped detector as opposed to once for each of the many detector elements.

In Fraunhofer diffraction particle sizing annular ring detector elements are advantageous, and an annular detector configured by switching to transparent a set of pixels in a circular pattern is also shown in FIG. 3. Note that as the detector transmission masks which can be produced with this concept will approach a perfect ring. Note also that the ring detector can be configured about any instantaneous center, a feature which is crucial for the use of laser diffraction particle sizing applications in combustion environments where refractive index gradients cause the incident laser beam to be deflected causing catastrophic effects for fixed geometry ring detectors. In FIG. 3 the instantaneous center of the transmitted beam is measured by the indicated x-y position detector 380, is the manner discussed above so that the detector 400 may be aligned to the center of the beam.

This light valve array design can be used to create a detector of virtually any geometry. Thus, an instrument with some level of intelligence could interrogate the scattering pattern, determine those scattering angles at which the particle size information is maximized, and then reconfigure the detector 400 to sample more points (scattering angles) in those regions of most interest).

Several different means for producing the transmitting or absorbing pixels can be envisioned. A first prototype uses the Faraday effect which depends on the input light being linearly polarized. Liquid crystal light valves are another common technology which could be used to create a "light gate array" as required for this invention.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A particle sizing system for determining particle size distributions in liquids and gases in a particle field using Fraunhofer diffraction patterns, said particle sizing system comprising:

a means for illuminating said particle field with a Fraunhofer diffraction pattern, said Fraunhofer diffraction pattern having a center axis;

a transform lens which receives and focuses said Fraunhofer diffraction pattern from said particle field at its focal point to produce an output;

a transform plane which is fixed at the focal point of said transform lens, said transform plane comprising a spatial light modulator which physically separates different bands of light of said Fraunhofer diffraction pattern in order to produce an output by passing only light through concentric rings which are adjustable in radius and width about the diffraction pattern's center axis, said spatial light modulator thereby allowing adjustable detection of selective particle size distributions since light scattered by very large is concentrated about comparatively small angles from said center axis, while light scattered by comparatively small particles in the particle field goes into comparatively large angles about said center axis of said diffraction pattern from said transform lens;

a detector which receives and measures said Fraunhofer diffraction pattern from said transform plane at increments that are adjusted by said spatial light modulator to indicate thereby said particle size distribution by detecting magnitudes of discrete angular distributions of scattered light in said Fraunhofer diffraction pattern from said transform plane;

an on-line test means which tests said particle sizing system using a particle field sample with a known particle size distribution which is compared to detected particle size distributions measured by said detector, said particle field sample comprising a diffraction reticle which includes a transparent sheet with a particle array of circular apertures with said known particle size distribution;

a means for detecting the center axis of said Fraunhofer diffraction pattern from said transform plane, said detecting means outputting a detection signal; and a means for controlling said spatial light modulator and said detector, said controlling means receiving said detection signal from said detecting means, and physically moving said detector so that it is aligned with the center axis of said Fraunhofer diffraction pattern from said transform lens, said controlling means also adjusting said spatial light modulator to pass only light through concentric rings which are incrementally adjusted in radius and width about said center axis of said Fraunhofer diffraction pattern, said controlling means also receiving and displaying measurements made by said detector to indicate thereby said particle size distribution in said particle field.

2. A particle sizing system, as defined in claim 1, wherein said controlling means comprises:

a servomechanism which contains at least three pizoelectric transducers which are physically in contact with said detector to physically tilt it to be aligned with said center axis of said Fraunhofer diffraction pattern in response to a set of electrical adjustment signals; and a computer which is electrically connected with said servomechanism, said detector, said spatial light modulator and said detecting means, said computer receiving said detection signal from said detecting means and determining a location of the center axis of said Fraunhofer diffraction pattern therefrom, said computer then sending said set of electrical adjustment signals to said servomechanism to cause it to tilt said detector so that it is aligned with said center axis of said Fraunhofer diffraction pattern.

3. A particle sizing system, as defined in claim 2, wherein said illuminating means comprises:

a laser which produces an illuminating laser beam; and a first beam expander spatial filter which receives and expands said illuminating laser beam from said laser through a first slit to produce said Fraunhofer diffraction pattern for said particle field.

4. A particle sizing system, as defined in claim 3, wherein said on-line test means comprises:

a first beam splitter which receives and splits said illuminating beam from said laser and outputs thereby said illuminating beam to said first beam expander as well as a sample of said illuminating beam;

an acousto-optic modulator which receives and modulates said sample of said illuminating beam from said first beam splitter to produce thereby a modulated sample of said illuminating beam;

a second beam expander spatial filter which receives and expands said modulated sample of said illuminating beam through a second slit to produce an output which includes a Fraunhofer diffraction pattern of said modulated sample of said laser beam;

a diffraction reticle which intercepts said output of said second beam expander with said modulated sample with said known particle size distribution which is compared with the measurement made by said detector, said diffraction reticle producing an output thereby; and a beam combiner which receives and combines the output of the diffraction reticle with the Fraunhofer diffraction pattern of said first beam expander spatial filter to produce a combined beam which is directed towards said transform lens.

5. A particle sizing system, as defined in claim 4, wherein said detecting means comprises:

a second beam splitter which receives and splits said output of said transform lens to forward it to said transform plane while extracting a sample; and a photodiode array which receives and detects said sample from said second beam splitter to output thereby a detection signal which indicates an X and Y position of said output of said transform lens which, in turn, indicates to said computer the center axis of said Fraunhofer diffraction pattern.

6. A particle sizing system for determining particle size distributions in liquids and gases in a particle field using Fraunhofer diffraction patterns, said particle sizing system comprising:

a laser which produces an illuminating laser beam;

a first beam expander spatial filter which receives and expands said illuminating laser beam from said laser through a first slit to produce said Fraunhofer diffraction pattern for said particle field, said Fraunhofer diffraction pattern having a center axis;

a transform lens which receives and focuses said Fraunhofer diffraction pattern from said particle at its focal point to produce an output;

a transform plane which is fixed at the focal point of said transform lens, said transform plane comprising a spatial light modulator which physically separates different bands of light of said Fraunhofer diffraction pattern in order to produce an output by passing only light through concentric rings which are adjustable in radius and width about the diffraction pattern's center axis, said spatial light modulator thereby allowing adjustable detection of selective particle size distributions since light scattered by very large particles is concentrated about comparatively small angles from said center axis, while light scattered by comparatively small particles in the particle field goes into comparatively large angles about said center axis of said diffraction pattern from said transform lens;

a detector which receives and measures said Fraunhofer diffraction pattern from said transform plane at increments that are adjusted by said spatial light modulator to indicate thereby said particle size distributions by detecting magnitudes of discrete angular distributions of scattered light in said Fraunhofer diffraction pattern from said transform plane;

a first beam splitter which receives and splits said illuminating beam from said laser and outputs thereby said illuminating beam to said first beam expander as well as a sample of said illuminating beam;

an acousto-optic modulator which receives and modulates said sample of said illuminating beam from said first beam splitter to produce thereby a modulated sample of said illuminating beam;

a second beam expander spatial filter which receives and expands said modulated sample of said illuminating beam through a second slit to produce an output which includes a Fraunhofer diffraction pattern of said modulated sample of said laser beam;

a diffraction reticle which intercepts said output of said second beam expander spatial filter with said modulated, sample with said known particle size distribution which is compared with the measurement made by said detector, said diffraction reticle producing an output thereby;

a beam combiner which receives and combines the output of the diffraction reticle with the Fraunhofer diffraction pattern of said first beam expander spatial filter to produce a combined beam which is directed towards said transforms lens;

a second beam splitter which receives and splits said output of said transform lens to forward it to said transform plane while extracting a sample;

a photodiode array which receives and detects said sample from said second beam splitter to output thereby a detection signal which indicates an X and Y position of said output of said transform lens which, in turn, indicates the center axis of said Fraunhofer diffraction pattern; and a servomechanism which contains a least three piezoelectric transducers which are physically in contact with said detector to physically tilt the detector to be aligned with said center axis of said Fraunhofer diffraction pattern.

7. An on-line test system that tests an optical particle size distribution sensing system which illuminates a medium with an illuminating beam from a laser to produce a diffraction pattern of scattered light, said optical particle size distribution sensing system having a means for measuring said diffraction pattern of scattered light to determine therefrom a measured particle size distribution in said medium, said on-line test system comprising;

a first beam splitter which receives and splits said illuminating beam from said laser and outputs thereby a sample of said illuminating beam;

an acousto-optic modulator which receives and modulates said sample of said illuminating beam from said first beam splitter to produce thereby a modulated sample of said illuminating beam;

a beam expander spatial filter which receives and expands said modulated sample of said illuminating beam through a second slit to produce an output which includes a Fraunhofer diffraction pattern of said modulated sample of said laser beam;

a diffraction reticle which intercept said output of said beam expander spatial filter with said modulated sample with a known particle size distribution which is compared with the measurement made by said optical particle size distribution sensing system said diffraction reticle producing an output thereby; and a beam combiner which receives and combines the output of the diffraction reticle with the Fraunhofer diffraction pattern of said beam expander spatial filter to produce a combined beam which is directed towards said measuring means of said optical particle size distribution sensing system so that said measured particle size distribution produced by said particle size distribution sensing is compared with said known particle size distribution of said diffraction reticle to yield therefrom an indication of the optical particle size distribution sensing system's accuracy.

8. An on-line test system, as defined in claim 7, wherein said diffraction reticle comprises a transparent sheet with a particle array of circular apertures with said known particle size distribution.

* * * * *